United States Patent
Grover et al.

(10) Patent No.: US 11,259,885 B2
(45) Date of Patent: *Mar. 1, 2022

(54) DRIVE UNIT AND RACK DRAPE FOR ROBOTIC SURGICAL INSTRUMENTS

(71) Applicant: Covidien LP, Mansfield, MA (US)

(72) Inventors: Simon R. Grover, Cambridge (GB); Charles F. Kilby, Cambridgeshire (GB); Daniel L. Fuller, Haverhill (GB); Alistair Ward, Swavesey (GB)

(73) Assignee: Covidien LP, Mansfield, MA (US)

( * ) Notice: Subject to any disclaimer, the term of this patent is extended or adjusted under 35 U.S.C. 154(b) by 272 days.

This patent is subject to a terminal disclaimer.

(21) Appl. No.: 16/662,328

(22) Filed: Oct. 24, 2019

(65) Prior Publication Data

US 2020/0054407 A1 Feb. 20, 2020

Related U.S. Application Data

(63) Continuation of application No. 15/520,905, filed as application No. PCT/US2015/055220 on Oct. 13, 2015, now Pat. No. 10,610,314.

(Continued)

(51) Int. Cl.
*A61B 34/35* (2016.01)
*A61B 46/10* (2016.01)
(Continued)

(52) U.S. Cl.
CPC .............. *A61B 34/35* (2016.02); *A61B 34/30* (2016.02); *A61B 34/71* (2016.02); *A61B 46/10* (2016.02);

(Continued)

(58) Field of Classification Search
CPC .......... A61B 34/71; A61B 2017/00407; A61B 2017/2923; F16H 19/04
See application file for complete search history.

(56) References Cited

U.S. PATENT DOCUMENTS

3,707,964 A 1/1973 Patience et al.
3,968,792 A 7/1976 Small
(Continued)

FOREIGN PATENT DOCUMENTS

CN 101426412 A 5/2009
CN 103655089 A 3/2014
(Continued)

OTHER PUBLICATIONS

"Surgical Sockinette", Surgical & Acute Care Catalog, p. 22.
(Continued)

*Primary Examiner* — Robert A Lynch
*Assistant Examiner* — Lindsey Bachman
(74) *Attorney, Agent, or Firm* — Carter, DeLuca & Farrell LLP (57) ABSTRACT

A surgical instrument is configured for coupling with an instrument drive unit that drives an actuation of the surgical instrument and operatively supports the surgical instrument. The surgical instrument includes a housing, an elongate body extending distally from the housing, an end effector extending distally from the elongate body, and a plurality of driven members rotatably fixed and longitudinally moveable relative to the elongate body. The plurality of driven members are longitudinal moveable relative to one another. Each driven member of the plurality of drive members is coupled to a respective cable that is attached to the end effector. The plurality of driven members is configured for engagement with an instrument drive unit.

19 Claims, 12 Drawing Sheets

Related U.S. Application Data (60) Provisional application No. 62/067,644, filed on Oct. 23, 2014.

(51) Int. Cl.
  *A61B 34/30* (2016.01)
  *A61B 34/00* (2016.01)
  *F16H 19/04* (2006.01)
  *A61B 17/00* (2006.01)

(52) U.S. Cl.
  CPC .............. *F16H 19/04* (2013.01); *A61B 34/74* (2016.02); *A61B 2017/00477* (2013.01)

(56) References Cited

U.S. PATENT DOCUMENTS

| | | |
|---|---|---|
| 3,982,307 A | 9/1976 | Smith et al. |
| 4,308,864 A | 1/1982 | Small et al. |
| 4,647,643 A | 3/1987 | Zdrahala et al. |
| 5,018,266 A | 5/1991 | Hutchinson et al. |
| 5,184,601 A | 2/1993 | Putman |
| 5,224,679 A | 7/1993 | Code |
| 5,441,042 A | 8/1995 | Putman |
| 5,498,230 A | 3/1996 | Adair |
| 5,631,973 A | 5/1997 | Green |
| 5,785,643 A | 7/1998 | Lynn |
| 5,876,328 A | 3/1999 | Fox et al. |
| 5,931,832 A | 8/1999 | Jensen |
| 6,063,095 A | 5/2000 | Wang et al. |
| 6,102,044 A | 8/2000 | Naidyhorski |
| 6,102,850 A | 8/2000 | Wang et al. |
| 6,132,368 A | 10/2000 | Cooper |
| 6,773,062 B2 | 8/2004 | Illulian |
| 7,297,142 B2 | 11/2007 | Brock |
| 7,666,191 B2 | 2/2010 | Orban, III et al. |
| 7,727,244 B2 | 6/2010 | Orban, III et al. |
| 8,202,278 B2 | 6/2012 | Orban, III et al. |
| 8,220,468 B2 | 7/2012 | Cooper et al. |
| 8,578,571 B2 | 11/2013 | Schmidt et al. |
| 8,746,252 B2 | 6/2014 | McGrogan et al. |
| 9,161,816 B2 | 10/2015 | Ball et al. |
| 9,295,521 B2 | 3/2016 | Pack et al. |
| 9,320,568 B2 | 4/2016 | Orban, III et al. |
| 2002/0138082 A1 | 9/2002 | Brock et al. |
| 2006/0235436 A1 | 10/2006 | Anderson et al. |
| 2007/0250073 A1 | 10/2007 | Brock et al. |
| 2009/0248039 A1 | 10/2009 | Cooper et al. |
| 2009/0314321 A1 | 12/2009 | Van Dyken |
| 2010/0170519 A1 | 7/2010 | Romo et al. |
| 2010/0175701 A1 | 7/2010 | Reis et al. |
| 2011/0290853 A1* | 12/2011 | Shelton, IV ......... A61B 17/072 227/177.1 |
| 2012/0150192 A1 | 6/2012 | Dachs, II et al. |
| 2012/0232566 A1 | 9/2012 | Orban, III et al. |
| 2013/0061857 A1 | 3/2013 | McNally et al. |
| 2013/0104909 A1 | 5/2013 | Barrier et al. |
| 2014/0252071 A1 | 9/2014 | Moore et al. |
| 2014/0338676 A1 | 11/2014 | Marinchak |
| 2015/0202009 A1 | 7/2015 | Nussbaumer et al. |

FOREIGN PATENT DOCUMENTS

| | | |
|---|---|---|
| CN | 103889359 A | 6/2014 |
| WO | 2013059432 A1 | 4/2013 |
| WO | 2015142824 A1 | 9/2015 |

OTHER PUBLICATIONS

Draping & Dressing Usag, Surgical & Acute Care Catalog, p. 24.
European Search Report dated May 22, 2018, in EP Appln. No. 15853552.
Chinese Office Action dated Dec. 5, 2018 issued in CN Appln. No. 201580055976.
International Search Report for PCT/US2015/055220, dated Jan. 18, 2016 (6 pages).

\* cited by examiner

DRIVE UNIT AND RACK DRAPE FOR ROBOTIC SURGICAL INSTRUMENTS

CROSS-REFERENCE TO RELATED APPLICATIONS

This application is a Continuation application which claims the benefit of and priority to U.S. patent application Ser. No. 15/520,905, filed on Apr. 21, 2017, which is a U.S. National Stage Application filed under 35 U.S.C. § 371(a) of International Patent Application Serial No. PCT/US2015/055220, filed Oct. 13, 2015, which claims the benefit of and priority to U.S. Provisional Patent Application Ser. No. 62/067,644, filed Oct. 23, 2014, the entire disclosure of which are incorporated by reference herein.

BACKGROUND

Robotic surgical systems have been used in minimally invasive medical procedures. Some robotic surgical systems include a console supporting a robot arm and a surgical instrument or at least one end effector that includes forceps or a grasping tool that is mounted to the robot arm. The robot arm provides mechanical power to the surgical instrument for its operation and movement. Each robot arm may include an instrument drive unit that is operatively connected to the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult. Further, cables for actuating functions of the surgical instrument can become entangled upon rotation of the surgical instrument relative to the instrument drive unit.

Therefore, there is a need for an instrument drive unit having a minimized size, that allows for greater degrees of freedom for an attached surgical instrument, and that provides for an easier removal and attachment of a surgical instrument. Additionally, since the surgical instrument and the instrument drive units are often reusable, there is a need to minimize possible contamination of the instrument drive unit.

SUMMARY

In accordance with an aspect of the present disclosure, a surgical assembly is provided. The surgical assembly includes a surgical instrument and an instrument drive unit configured for actuation of the surgical instrument. The surgical instrument may include a housing, an elongate body extending distally from the housing, an end effector extending distally from the elongate body, and first and second circular racks rotatably fixed and longitudinally movable relative to the elongate body, wherein the first circular rack is slidably receivable within the second circular rack. The instrument drive unit may be configured to operatively and releasably support the surgical instrument. The instrument drive unit may include a first drive motor operably connected to the first circular rack for longitudinally moving the first circular rack relative to the elongate body and a second drive motor operably connected to the second circular rack for longitudinally moving the second circular rack relative to the elongate body.

In embodiments, the surgical instrument includes a first cable extending distally from the first circular rack and a second cable extending distally from the second circular rack. Each cable may operably extend to the end effector of the surgical instrument. The first drive motor may include a first drive gear for engaging the first circular rack and the second drive motor may include a second drive gear for engaging the second circular rack.

In some embodiments, the surgical assembly includes third and fourth circular racks. The fourth circular rack may be slidably receivable within the third circular rack. The instrument drive unit of these embodiments include a third motor for operable connection to the third circular rack and a fourth motor for operable connection to the fourth circular rack. The surgical assembly includes a third cable extending distally from the third circular rack and a fourth cable extending distally from the fourth circular rack.

In embodiments, the surgical instrument further includes a first rotation gear fixedly supported on the elongate body for facilitating rotation of the elongate body about a longitudinal axis of the elongate body. The instrument drive unit may include a first rotation motor for operable connection to the first rotation gear for effecting rotation of the elongate body about the longitudinal axis of the elongate body. The instrument drive unit may include a first rotation gear connected to the first rotation motor and operably connected to the first rotation gear of the surgical instrument for effecting rotation of the elongate body about the longitudinal axis of the elongate body. The first rotation gear may include a plurality of openings for slidably receiving cables therethrough.

Embodiments of the instrument drive unit may include a housing and a pair of flanges extending outwardly from the housing of the instrument drive unit. Each flange may define a recess for selectively receiving the surgical instrument such that the surgical instrument is offset from the housing of the instrument drive unit. The instrument drive unit may include a pair of latches for selectively securing the surgical instrument within the recesses formed in the flanges of the instrument drive unit.

Embodiments of surgical assemblies may include a protective barrier operably received between the instrument drive unit and the surgical instrument. The protective barrier may include a belt configured for alignment with the first and second circular racks of the surgical instrument when the surgical instrument is engaged with the instrument drive unit. The protective barrier may be dimensioned to cover at least the instrument drive unit.

Another embodiment of a surgical assembly includes a surgical instrument, an instrument drive unit and a protective barrier received between the surgical instrument and the instrument drive unit. The protective barrier may include a belt configured for alignment with the first and second circular racks of the surgical instrument when the surgical instrument is engaged with the instrument drive unit. The belt of the protective barrier may include a textured surface to facilitate engagement with the first and second circular racks of the surgical instrument. The protective barrier may be dimensioned to cover at least the instrument drive unit.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about plus or minus ten degrees (+/−10°).

BRIEF DESCRIPTION OF THE DRAWINGS

Embodiments of the present disclosure are described herein with reference to the accompanying drawings, wherein.

DETAILED DESCRIPTION

Embodiments of the presently disclosed surgical assembly including an instrument drive unit and a surgical instrument and methods thereof are described in detail with reference to the drawings, in which like reference numerals designate identical or corresponding elements in each of the several views. As used herein the term "distal" refers to that portion of the surgical instrument and/or instrument drive unit that is closer to the patient, while the term "proximal" refers to that portion of the surgical instrument and/or instrument drive unit that is farther from the patient.

Figure 1:
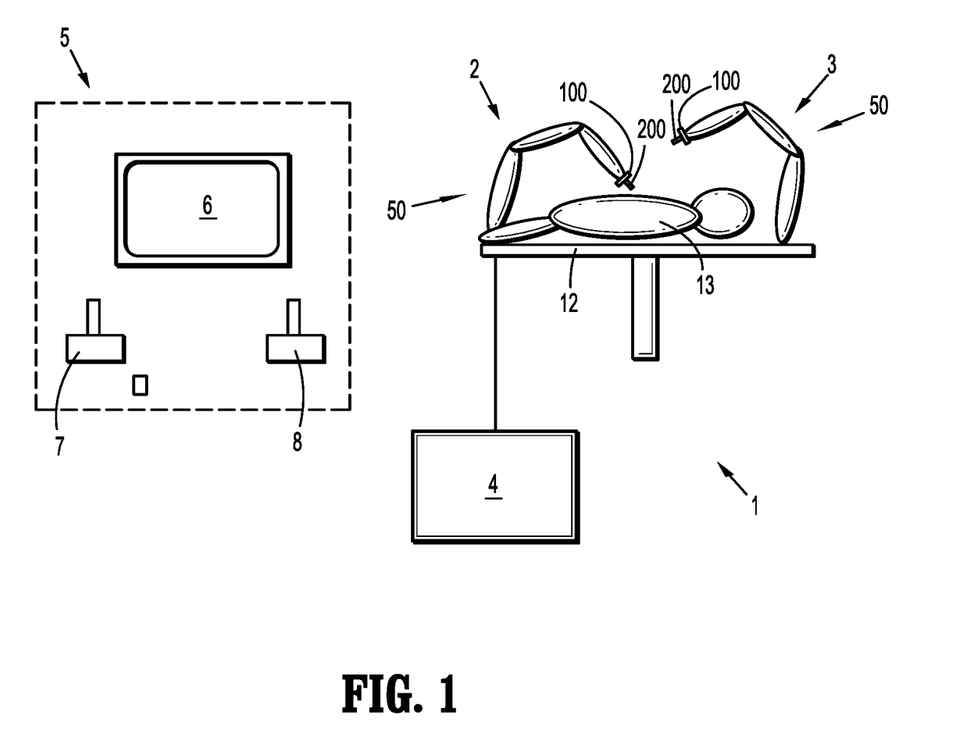
FIG. 1 is a schematic illustration of a robotic surgical system in accordance with the present disclosure.

Referring initially to FIG. 1, a surgical system, such as, for example, a robotic surgical system is shown generally as surgical system 1 and generally includes a plurality of robotic arms 2, 3, a control device 4, and an operating console 5 coupled with control device 4. Operating console 5 includes a display device 6, which is set up in particular to display three-dimensional images, and manual input devices 7, 8, by means of which a person (not shown), for example a surgeon, is able to telemanipulate robotic arms 2, 3 in a first operating mode, as known in principle to a person skilled in the art. Each of the robotic arms 2, 3 is composed of a plurality of members, which are connected through joints.

Surgical system 1 may also include an instrument drive unit 100 connected to distal ends of each of robotic arms 2, 3. A surgical instrument 200 supporting a tool assembly (not shown), e.g., graspers, forceps, stapling unit may be attached to instrument drive unit 100. Each robotic arm 2, 3 and its respective drive unit 100 and surgical instrument 200 in accordance with the embodiments disclosed herein, as will be described in greater detail below, are collectively referred to as surgical assembly 50.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their instrument drive units 100 and thus the surgical instrument 200 (including an attached tool assembly) execute a desired movement according to a movement defined by means of manual input devices 7, 8. Control device 4 may also be set up in such a way that it regulates the movement of robotic arms 2, 3 and/or of the drives.

Surgical system 1 is configured for use on a patient 13 lying on a patient table 12 to be treated in a minimally invasive manner by means of a tool assembly. Surgical system 1 may also include more than two robotic arms 2, 3, the additional robotic arms likewise being connected to control device 4 and being telemanipulatable by means of operating console 5. A surgical instrument 200, including a tool assembly (not shown) may also be attached to the additional robotic arm.

Reference may be made to U.S. Patent Publication No. 2012/0116416, filed on Nov. 3, 2011, entitled "Medical Workstation," the entire content of which is incorporated herein by reference, for a detailed discussion of the construction and operation of an exemplary surgical system.

Figure 2:
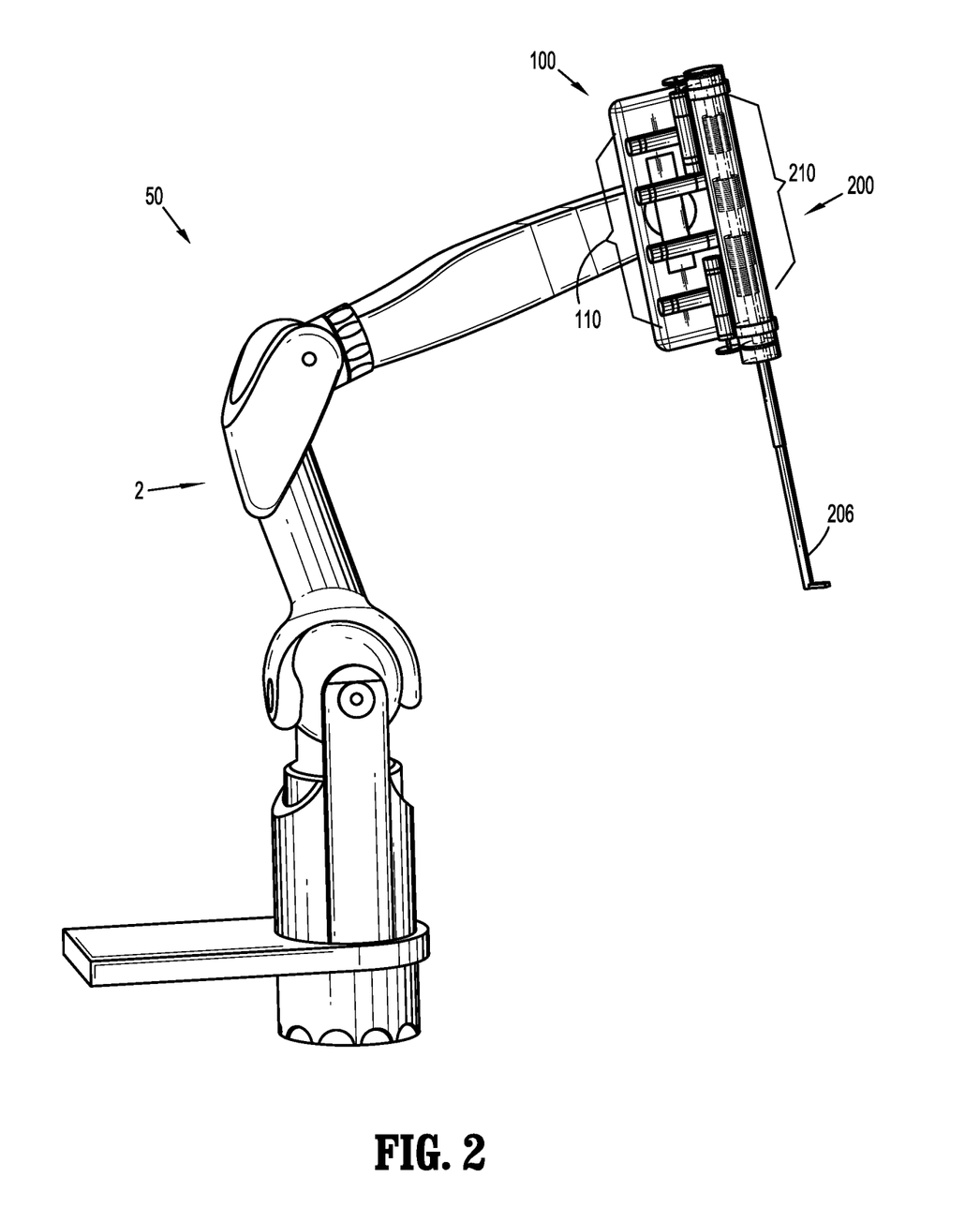
FIG. 2 is a perspective view of a surgical assembly, in accordance with an embodiment of the present disclosure, illustrated being attached to a robot arm of a robotic surgical system.

A surgical assembly 50, which includes at least one robotic arm, e.g., robotic arm 2, an instrument drive unit 100 connected to robotic arm 2, and surgical instrument 200 coupled with or to instrument drive unit 100, is illustrated in FIG. 2. As will be described in further detail below, surgical instrument 200 is side loaded into instrument drive unit 100. Specifically, to attach surgical instrument 200 with instrument drive unit 100, surgical instrument 200 is positioned adjacent instrument drive unit 100 such that various components of surgical instrument 200 align with corresponding components of instrument drive unit 100. Instrument drive unit 100 is subsequently moved into engagement with instrument drive unit 100 and selectively secured to instrument drive unit 100. In an alternative embodiment, a protective barrier or drape 300 (FIGS. 12-14) is received over instrument drive unit 100 prior to engaging surgical instrument 200 with instrument drive unit 100 to separate surgical instrument 200 from instrument drive unit 100.

Instrument drive unit 100 is configured for driving an actuation of a tool assembly (not shown) of surgical instrument 200 and to operatively support surgical instrument 200 therein. Instrument drive unit 100 transfers power from motors 110 to surgical instrument 200 to drive movement of cables 230 (FIG. 7) that are attached to the tool assembly. Instrument drive unit 100 includes a plurality of driving members, such as, for example, drive gears 112 (FIG. 3), operably engaged with respective drive motors 110. Drive motors 110 operably engage circular racks 210 of surgical instrument 200 to independently longitudinally move circular racks 210 with respect to one another. Circular racks 210 convert rotational movement from drive motors 110 into longitudinal movement to push and/or pull cables 230 (FIG. 7) of surgical instrument 200 to actuate or carry out certain functions of the tool assembly (not shown) secured to end effector 206.

Figure 3:
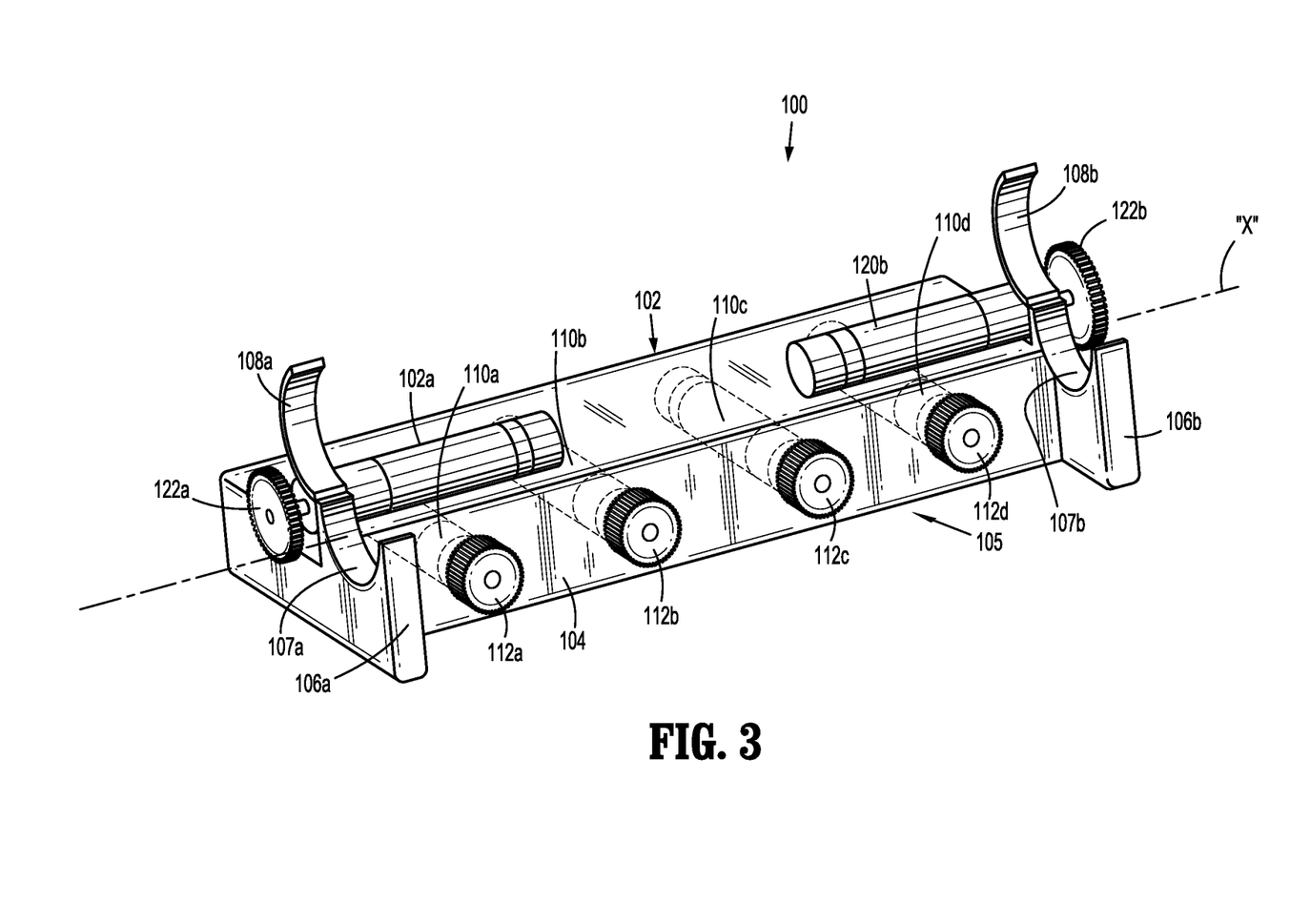
FIG. 3 is a side perspective view of an instrument drive unit of the surgical assembly shown in FIG. 2.

With reference to FIG. 3, instrument drive unit 100 includes a platform or housing 102 for supporting various components of instrument drive unit 100 and for connecting instrument drive unit 100 to robotic arm 2. For a detail description of the connection of housing 102 to robotic arm 2 please refer to commonly owned U.S. Patent Application Ser. No. 61/992,700, filed May 13, 2014, the content of which is incorporated by reference herein in its entirety.

Instrument drive unit 100 includes a set of drive motors 110a, 110b, 110c, 110d (collectively, drive motors 110) and a set of rotation motors 120a, 120b (collectively, rotation motors 120). Drive motors 110 are spaced along a longitudinal axis "X" of housing 102 and extend perpendicular thereto. Each drive motor 110a, 110b, 110c, 110d includes a drive gear 112a, 112b, 112c, 112d, respectively, extending from a lateral side wall 104 of housing 102. As will be described in further detail below, drive gears 112 are positioned to engage circular racks 210 of surgical instrument 200 to independently move circular racks 210 longitudinally with respect to one another. More particularly, when surgical instrument 200 is secured to instrument drive unit 100 in a first configuration (FIG. 6), i.e., with end effector 206 extending in a first direction from housing 102 of instrument drive unit 100, drive gears 112a, 112b, 112c, 112d of instrument drive unit 100 engage respective circular racks 210a, 210b, 210c, 210d of surgical instrument 200, and when surgical instrument 200 is secured to instrument drive unit 100 in a second configuration (not shown), i.e., with end effector 206 extending in a second direction from housing 102 of instrument drive unit 100, drive gears 112a, 112b, 112c, 112d of instrument drive unit 100 engage respective circular racks 210d, 210c, 210b, 210a of surgical instrument 200. Although shown having four (4) drive motors 110 and four (4) corresponding drive gears 112, it is envisioned that instrument drive unit 100 may include any number of drive motors to accommodate any number of circular racks 210 within surgical instrument 200. For example, instrument drive unit 100 may include only two (2) drive motors 110 or may include six (6) drive motors.

Rotation motors 120a, 120b are received within opposite ends of housing 102 and each includes a drive gear 122a, 122b, respectively, disposed adjacent the respective proximal and distal ends of housing 102 of instrument drive unit 100. As will be described in further detail below, rotation gears 122 are positioned to engage rotational gears 220 of surgical instrument 200. More particularly, when surgical instrument 200 is secured to instrument drive unit 100 in the first configuration (FIG. 6), rotation gears 122a, 122b of instrument drive unit 100 engage respective rotational gears 220a, 220b of surgical instrument 200, and when surgical instrument 200 is secured to instrument drive unit 100 in the second configuration (not shown), drive gears 122a, 122b of instrument drive unit 100 engage respective rotational gears 220b, 220a of surgical instrument 200.

Housing 102 of instrument drive unit 100 is configured to selectively and operably receive surgical instrument 200 in an offset configuration. In particular, instrument drive unit 100 includes a pair of flanges 106a, 106b extending outwardly from a lateral side wall 104 of housing 102 and about drive gears 112 of respective drive motors 110 to form a longitudinal opening 105. Each flange 106a, 106b defines a semi-circular recesses 107a, 107b, respectively, for selectively receiving housing 202 of surgical instrument 200 within longitudinal opening 105. Flanges 106a, 106b and respective recesses 107a, 107b are configured to receive surgical instrument 200 in the first configuration (FIG. 6) or in the second configuration (not shown). In this manner, when surgical instrument 200 is received within recesses 107a, 107b of flanges 106a, 106b, respectively, and longitudinal opening 105 formed between flanges 106a, 106b, circular racks 210 of surgical instrument 200 engage drive gears 112 of instrument drive unit 100 and rotational gears 220 of surgical instrument 200 engage rotation gears 122 of instrument drive unit 100. Latches 108a, 108b are positioned on housing 102 of instrument drive unit 100 for selectively securing surgical instrument 200 within recesses 107a, 107b, respectively, of respective flanges 106a, 106b and to instrument drive unit 100.

Figure 4:
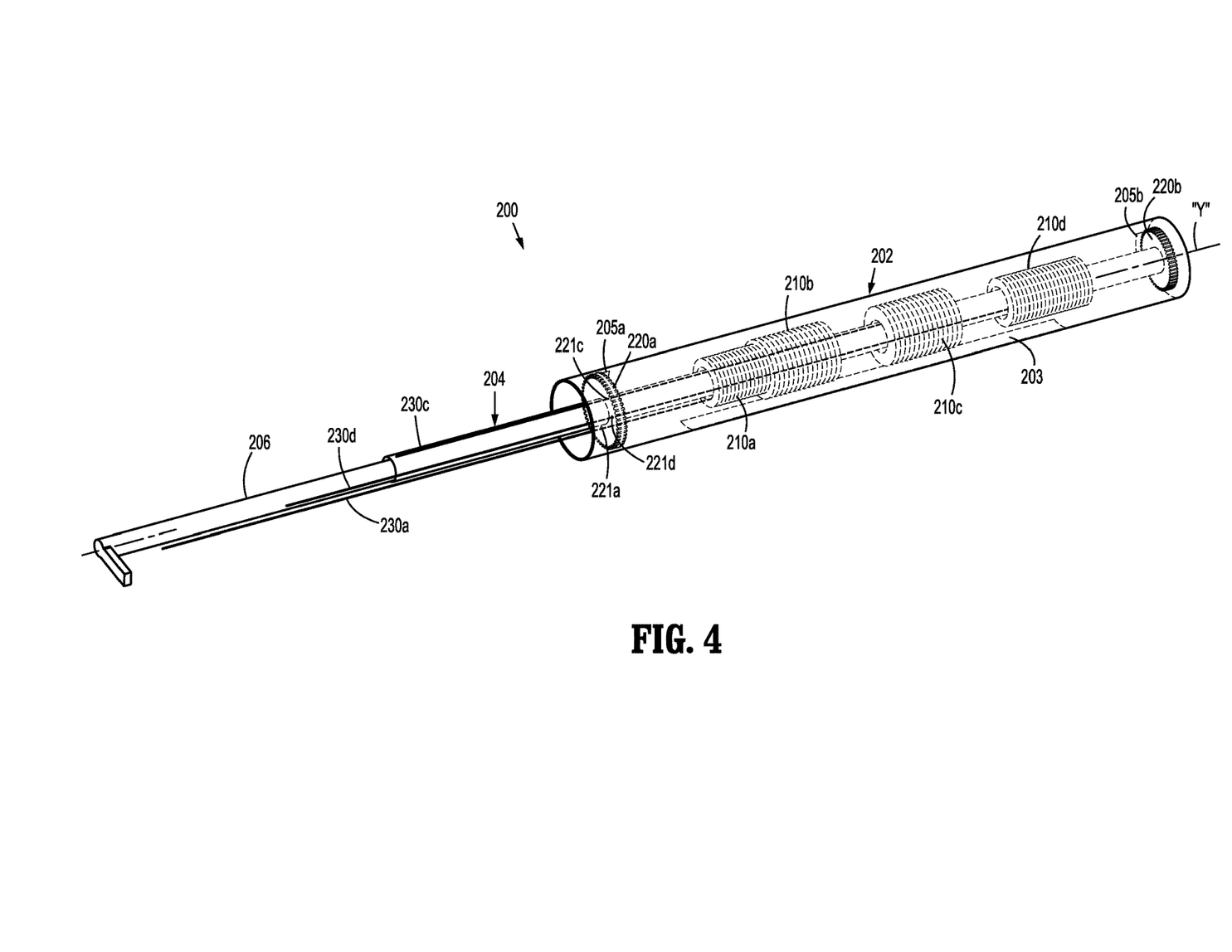
FIG. 4 is a side perspective view of a surgical instrument of the surgical assembly shown in FIG. 2.

With reference now to FIG. 4, surgical instrument 200 includes an elongate housing 202 and an elongate body 204 rotatably supported within and extending distally from elongate housing 202. An end effector 206 extends through and distally from elongate body 204. End effector 206 is rotatable relative to elongate body 204 along longitudinal axis "Y" of surgical instrument 200 and is configured to selectively receive a tool assembly (not shown), e.g., grasper, vessel sealer, stapling unit. A rotary drive member (not shown) may extend through end effector 206 for providing a rotary motion to the tool assembly (not shown) received on the tool assembly.

Surgical instrument 200 includes circular racks 210a, 210b, 210c, 210d and rotational gears 220a, 220b. Circular racks 210a, 210b, 210c, 210d are rotationally fixed and longitudinal movable on elongate body 204 of surgical instrument 200. More particularly, circular racks 210a, 210b, 210c, 210d are independently movable along a longitudinal axis "Y" of housing 102. Circular racks 210a, 210d are sized and dimensioned to be received within respective circular racks 210b, 210c such that circular racks 210a, 210b and circular racks 210c, 210d can at least partially overlap. As will be described in further detail below, the overlapping of circular racks 210a, 210b and the overlapping of circular racks 210c, 210d permits a reduction in the overall length of surgical instrument 200 while maintaining the range of motion of circular racks 210 and the functionality of surgical instrument 200.

Housing 202 of surgical instrument 200 defines a longitudinal slot 203 through which drive gears 112a, 112b, 112c, 112d (FIG. 3) of respective motors 110a, 110b, 110c, 110d (FIG. 3) of instrument drive unit 100 extend when surgical instrument 200 is secured to instrument drive unit 100. As described above, when surgical instrument 200 is secured to the instrument drive unit 100 in the first configuration, drive gears 112a, 112b, 112c, 112d of instrument drive unit 100 are positioned to engage respective circular racks 210a, 210b, 210c, 210d of surgical instrument 200 to independently move circular racks 210a, 210b, 210c, 210d along longitudinal axis "Y" of surgical instrument 200 and when surgical instrument 200 is secured to the instrument drive unit 100 in the second configuration, drive gears 112a, 112b, 112c, 112d of instrument drive unit 100 are positioned to engage respective circular racks 210d, 210c, 210b, 210c of surgical instrument 200 to independently move circular racks 210d, 210c, 210b, 210a along longitudinal axis "Y" of surgical instrument 200.

Cables 230 extend distally from circular racks 210 of surgical instrument 200 to effect actuation and operation of a tool assembly (not shown) secured to a distal end of end effector 206. More particularly, a cable 230a is secured to and extends from circular rack 210a, a cable 230b is secured to and extends from circular rack 210b, a cable 230c is secured to and extends from circular rack 210c, and a cable 230d is secured to and extends from circular rack 210d. Longitudinal movement of circular racks 210a, 210b, 210c, 210d cause corresponding longitudinal movement of respective cables 230a, 230b, 230c, 230d. As noted above, circular racks 210a, 210b, 210c, 210d are independently moveable relative to each other such that respective cables 230a, 230b, 230c, 230d may be pushed or pulled relative to each other.

Distal ends of cables 230 operably connect to a tool assembly (not shown) to effect actuation and operation thereof. Commonly owned U.S. patent application Ser. No. 14/257,063, filed Apr. 21, 2014, and entitled "Adapter Assembly with Gimbal for Interconnecting Electromechanical Surgical Devices and Surgical Loading Units, and Surgical Systems Thereof," the entire contents of which are hereby incorporated by reference, describes surgical stapling devices with tool assemblies that support distally advanceable sleds operatively coupled to a rotatable lead screw to fire surgical staples. It is contemplated that cables $230_a$, $230_b$, $230_c$, $230_d$ can operatively couple to the tool assembly, for example, similar to the gimbal assembly described in U.S. patent application Ser. No. 14/257,063, filed Apr. 21, 2014 (now U.S. Pat. No. 10,080,552).

Although shown and described as being cables 230, it is envisioned that rods (not shown) or other connection means may be secured to and extend from circular racks 210 to effect actuation and operation of the tool assembly. As noted above, alternative embodiments of surgical instrument 200 may have more or less than four (4) circular racks 210 and, therefore, may include more or fewer than four (4) cables 230.

Figure 6:
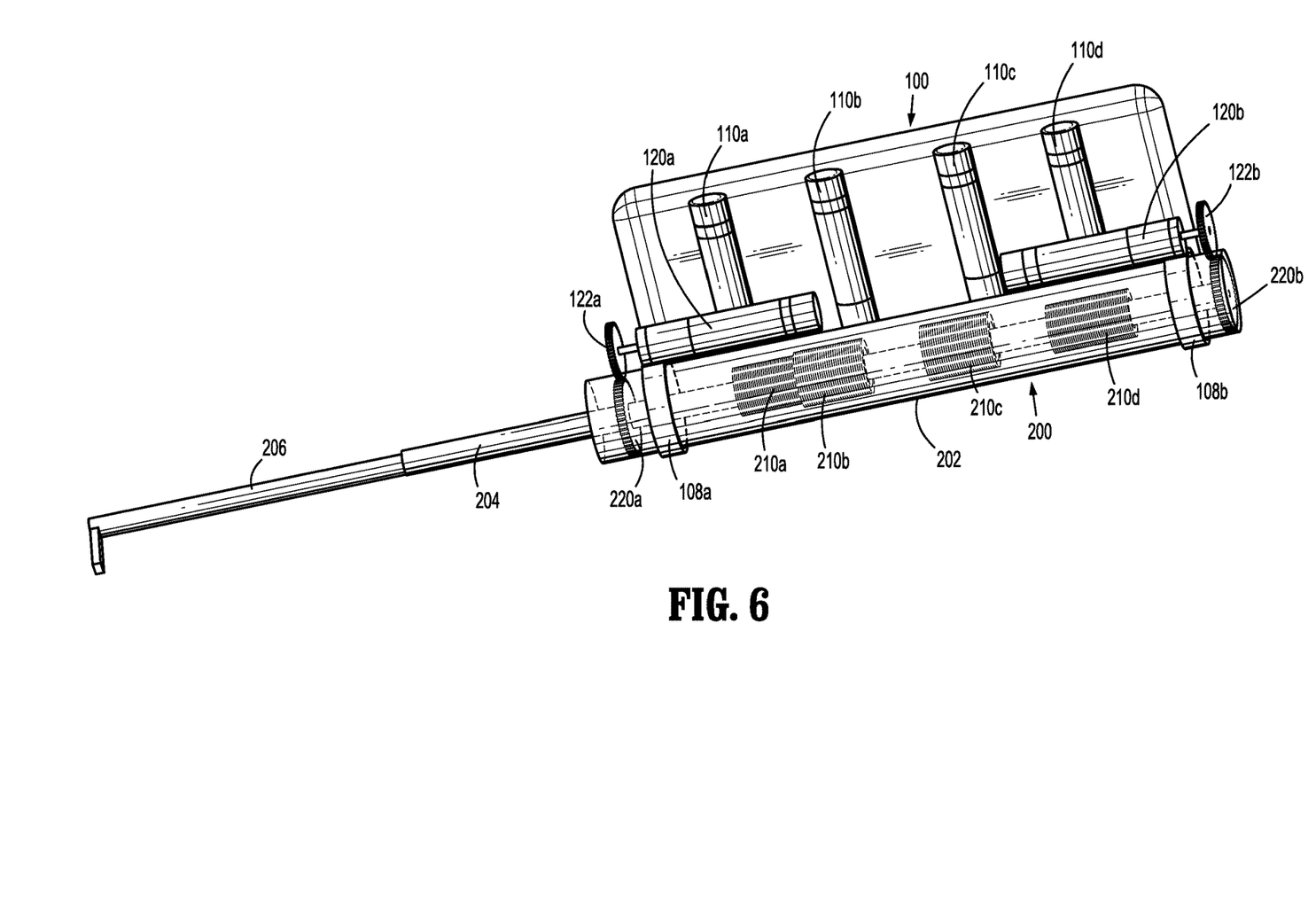
FIG. 6 is a top perspective view of the instrument drive unit shown in FIG. 3 and the surgical instrument shown in FIG. 4, subsequent to attachment of the surgical instrument to the instrument drive unit.

Distal rotational gear 220a of surgical instrument 200 is fixedly secured to elongate body 204 and proximal rotational gear 220b is fixedly secured to end effector 206 or to a rotary drive member (not shown) extending through end effector 206. Distal and proximal rotational gears 220a, 220b are positioned to be received through slots 205a, 205b, respectively, formed in housing 202 when surgical instrument 200 is secured to instrument drive unit 100 in the first configuration (FIG. 6). When surgical instrument 200 is secured to instrument drive unit 100 in the second configuration (not shown), distal and proximal rotational gears 220a, 220b of surgical instrument 200 are positioned to be received through slots 205a, 205b (FIG. 4), respectively. As described above, depending on the orientation of surgical instrument 200 relative to instrument drive unit 100, one of rotation gears 122a, 122b of instrument drive unit 100 is positioned to engage rotational gear 220a of surgical instrument 200 to rotate elongate body 204 about longitudinal axis "Y" and the other of rotation gears 122a, 122b of instrument drive unit 100 is configured to engage rotational gear 220b of surgical instrument 200 to rotate end effector 206 and/or the rotary drive member (not shown) about longitudinal axis "Y".

Distal rotational gear 220a defines a plurality of openings 221a, 221b, 221c, 221d for slidably receiving respective cables 230a, 230b, 230c, 230d therethrough. In this manner, distal rotational gear 220a maintains cables 230 in a spaced apart relation during operation of surgical assembly 50 (FIG. 2) to prevent twisting and/or tangling of the cables 230. In embodiments of surgical instrument 200 with more than four (4) cables 230, first rotational gear 220a may include more than four (4) openings for accommodating the additional cables 230.

Figure 5:
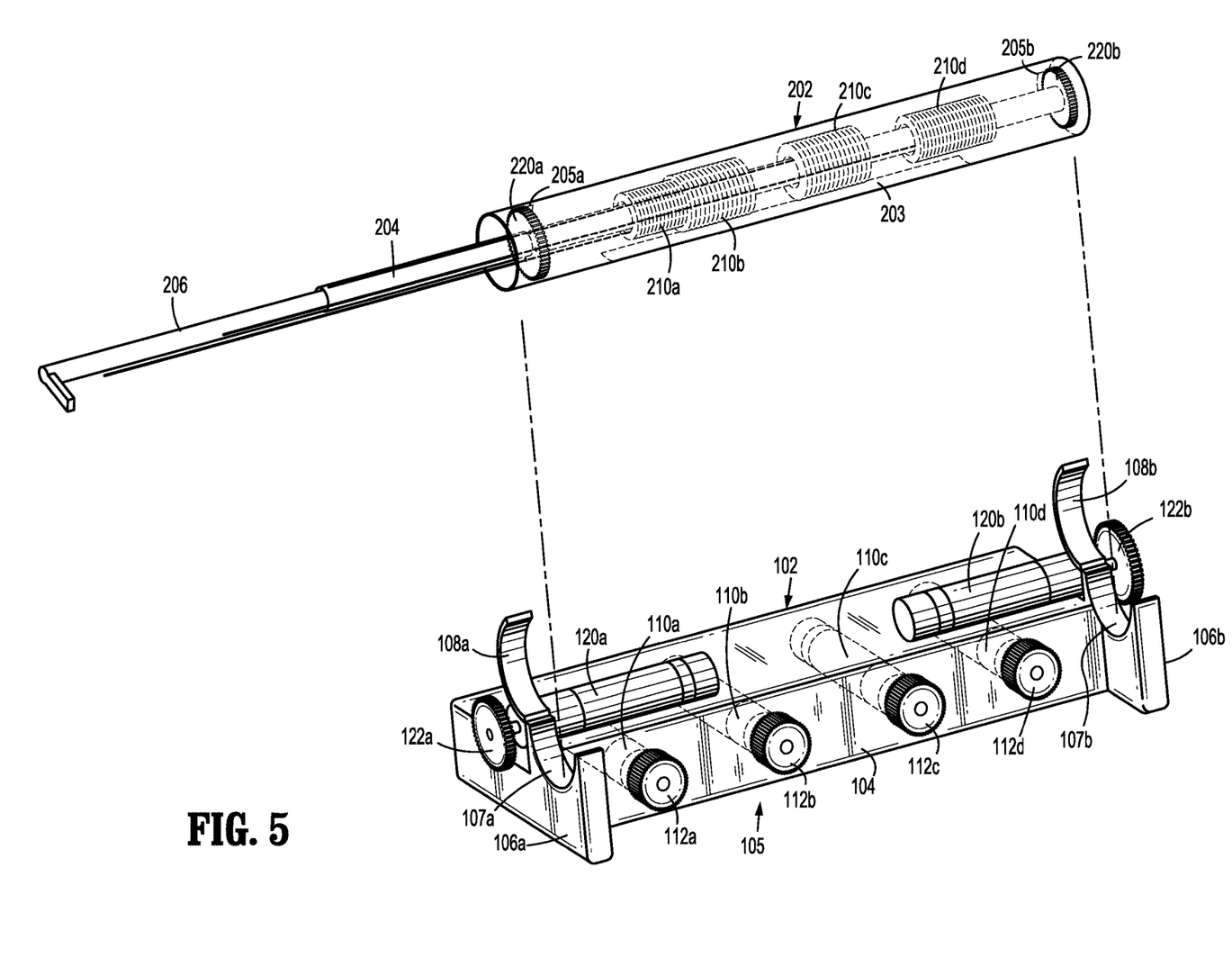
FIG. 5 is a side perspective view of the instrument drive unit shown in FIG. 3 and the surgical instrument shown in FIG. 4, prior to attachment of the surgical instrument to the instrument drive unit.
Figure 7:
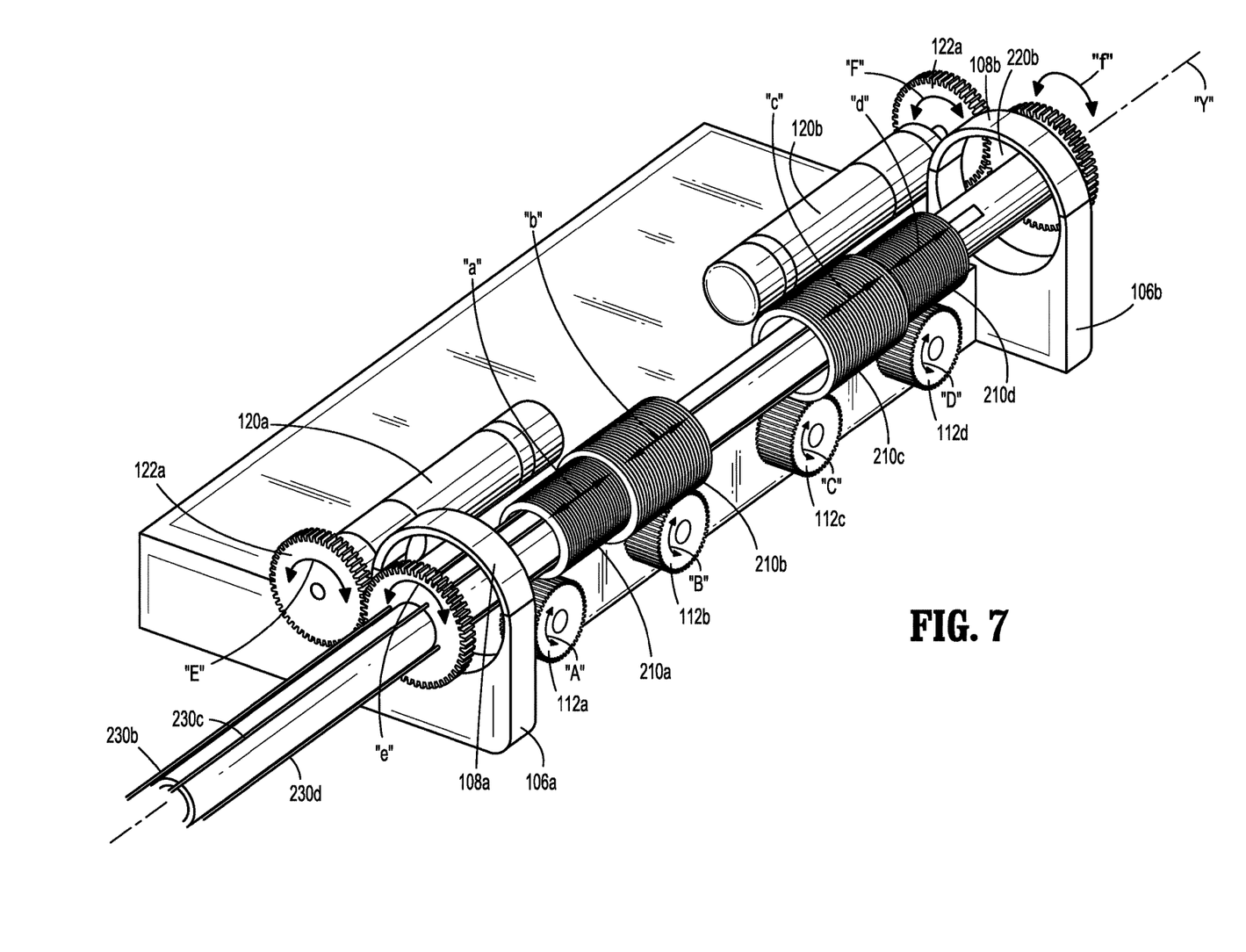
FIG. 7 is a front perspective view of the surgical instrument shown in FIG. 4 attached to the instrument drive unit shown in FIG. 3, with the housing of the surgical instrument removed.

With reference to FIGS. 5-7, surgical instrument 200 is secured to instrument drive unit 100 by first aligning the components of surgical instrument 200 with the components of instrument drive unit 100. With initial reference to FIG. 5, circular racks 210a, 210b, 210c, 210d are aligned with respective drive gears 112a, 112b, 112c, 112b of drive motors 110a, 110b, 110c, 110d, respectively, of instrument drive unit 100 and rotational gears 220a, 220b of surgical instrument 200 are aligned with respective rotation gears 122a, 122b of rotation motors 120a, 120b, respectively, of instrument drive unit 100. Alternatively, as described in detail above, surgical instrument 200 may be oriented relative to instrument drive unit 100 such that circular racks 210a, 210b, 210c, 210d are aligned with respective drive gears 112d, 112c, 112b, 112a of drive motors 110d, 110c, 110b, 110a, respectively, of instrument drive unit 100 and rotational gears 220a, 220b of surgical instrument 200 are aligned with respective rotation gears 122b, 122a of rotation motors 120b, 120a, respectively, of instrument drive unit 100.

Turning now to FIGS. 6 and 7, housing 202 of surgical instrument 200 is then received within recesses 107a, 107b formed in respective flanges 106a, 106b extending from lateral side wall 104 of housing 102 of instrument drive unit 100 such that housing 202 of surgical instrument 200 is received within longitudinal opening 105 of instrument drive unit 100. Receipt of housing 202 of surgical instrument 200 within recess 107a, 107b and longitudinal opening 105 of housing 102 of instrument drive unit 100 causes engagement of circular racks 210a, 210b, 210c, 210d of surgical instrument 200 with respective drive gears 112a, 112b, 112c, 112b of drive motors 110a, 110b, 110c, 110d, respectively, of instrument drive unit 100 and engagement of rotational gears 220a, 220b of surgical instrument 200 with respective rotation gears 122a, 122b of rotation motors 120a, 120b of instrument drive unit 100. Housing 202 of surgical instrument 200 is selectively secured within recesses 107a, 107b formed in respective flanges 106a, 106b of housing 102 of instrument drive unit 100 by latches 108a, 108b.

Instrument drive unit 100 may be attached to robotic arm 2 (FIG. 2) prior to or subsequent to attachment of surgical instrument 200 to instrument drive unit 100. As will be described in further detail below, a protective barrier or drape 300 (FIG. 13) may be received over instrument drive unit 100 prior to attaching surgical instrument 200 to instrument drive unit 100 to provide a sterile interface between instrument drive unit 100 and surgical instrument 200.

Once instrument drive unit 100 is secured to robotic arm 2 and surgical instrument 200 is secured to instrument drive unit 100, control device 4 is used to control the movement of robotic arm 2 and to actuate drive and rotation motors 110, 120 within instrument drive unit 100 to cause the positioning and actuation of the tool assembly (not shown) secured to end effector 206 of surgical instrument 200. More particularly, control device 4 may be operated to individually activate drive and rotation motors 110, 120 instrument drive unit 100 to longitudinal move circular racks 210 of surgical instrument 200 and rotate rotational gears 220a, 220b of surgical instrument 200, respectively, and thereby push and/or pull cables 230 of surgical instrument 200 and rotate elongate body 204 of surgical instrument 200, respectively.

As described above, individual activation of drive motors 110a, 110b, 110c, 110d causes the clockwise and/or counter-clockwise rotation of drive gears 112a, 112b, 112c, 112d, respectively, of instrument drive unit 100, as indicated by respective arrows "A", "B", "C", "D" shown in FIG. 7, which causes individual longitudinal movement of respective circular racks 210a, 210b, 210c, 210d of surgical instrument 200, as indicated by respective arrows "a", "b", "c", "d" shown in FIG. 7. As also described above, longitudinal movement of circular racks 210a, 210b, 210c, 210d of surgical instrument 200 causes the pushing and/or pulling of respective cables 230a, 230b, 230c, 230d to actuate a tool assembly (not shown) secured to end effector 206 of surgical instrument 200.

Individual or simultaneous activation of rotation motors 120a, 120b, to cause the clockwise and/or counter-clockwise rotation of respective rotation gears 122a, 122b, respectively, of instrument drive unit 100, as indicated by arrows "E", "F" in FIG. 7, causes the clockwise and/or counter-clockwise rotation of respective rotational gears 220a, 220b, as indicated by arrows "e", "f" shown in FIG. 7, to cause the independent or simultaneous clockwise and/or counter-clockwise rotation of elongate body 204, end effector 206 and/or a rotary drive member (not shown) extending through end effector 206 about longitudinal axis "Y".

Figure 8:
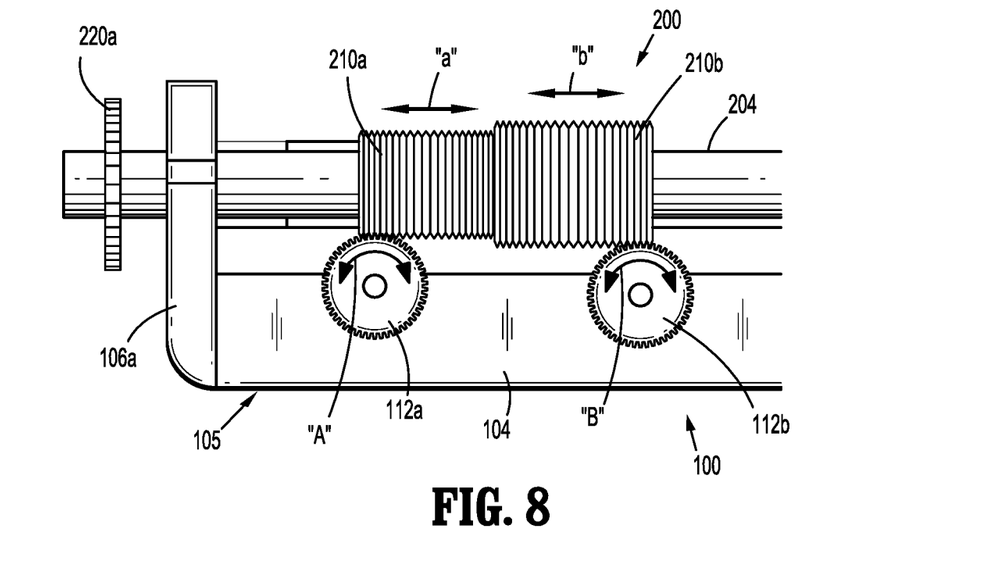
FIG. 8 is an enlarged side view of a first and second circular rack of the surgical instrument shown in FIG. 4 engaged with a first and second drive gear of the instrument drive unit shown in FIG. 3, with the first circular rack partially received within the second circular rack.
Figure 9:
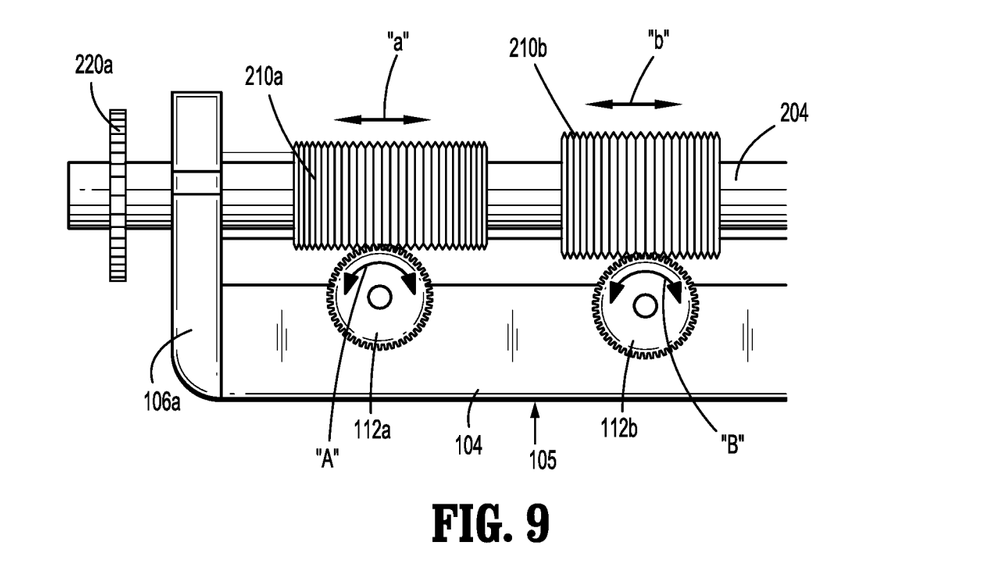
FIG. 9 is an enlarged side view of the first and second circular racks and the first and second drive gears shown in FIG. 8, with the first and second circular racks in spaced apart relation.

As illustrated in FIGS. 8 and 9, circular racks 210a, 210b of surgical instrument 200 are arranged such that circular rack 210a is receivable within circular rack 210b. In this manner, the distance each of circular racks 210a, 210b can be moved relative to each other is maximized while minimizing the length of housing 202 of surgical instrument 200. Circular racks 210c, 210d of surgical instrument 200 are arranged in a similar manner to offer the same benefit.

Figure 10:
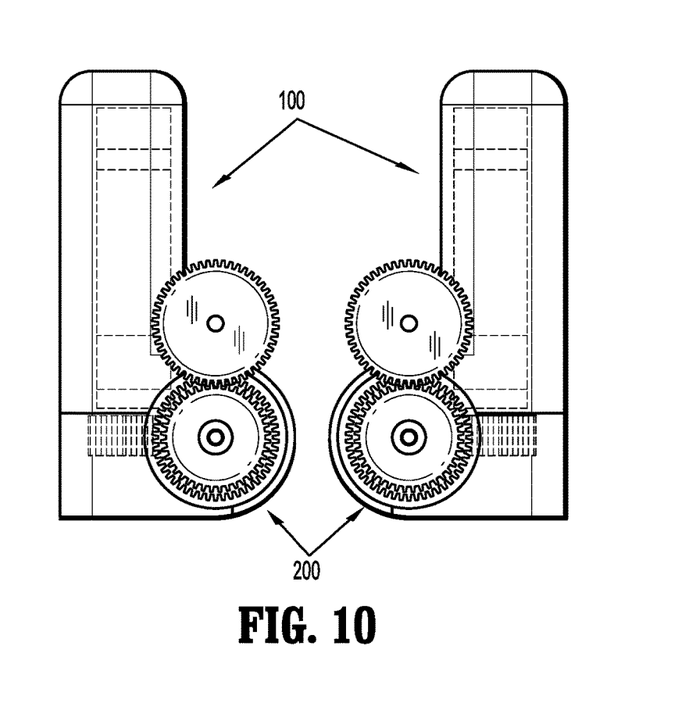
FIG. 10 is an end view of a first instrument drive unit and surgical instrument positioned adjacent to and parallel with a second instrument drive unit and surgical instrument.
Figure 11:
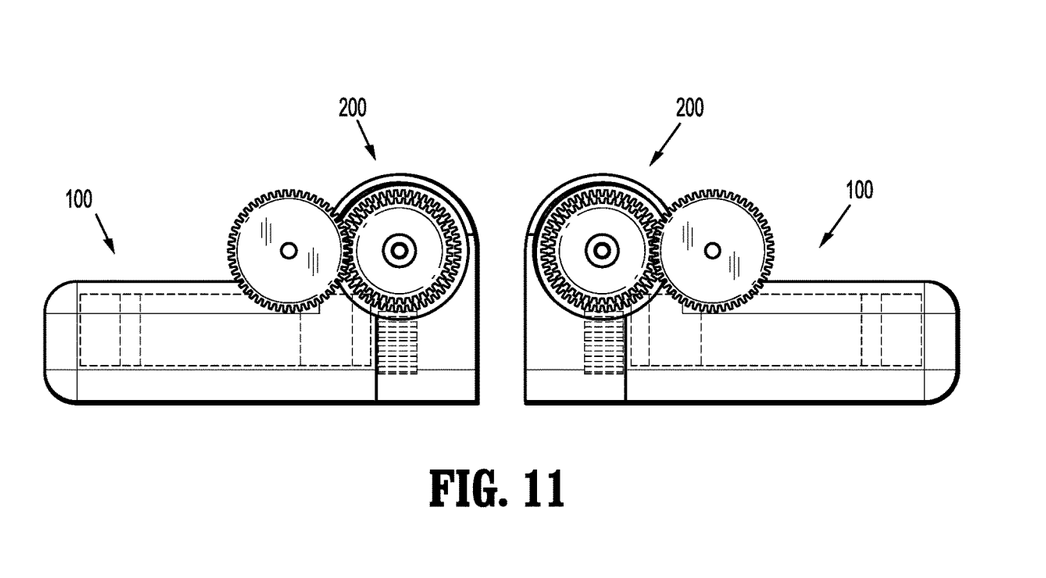
FIG. 11 is an end view of the first instrument drive unit and surgical instrument and the second instrument drive unit and surgical instrument shown in FIG. 10, in another adjacent and parallel configuration.

With reference now to FIGS. 10 and 11, the offset positioning of surgical instrument 200 relative to instrument drive unit 100 allows for greater workspace access as the surgical instruments 200 can be placed in close parallel proximity to one another. As illustrated in FIG. 10, surgical instruments 200 can be positioned in close parallel proximity to one another as housing 102 of instrument drive units 100 extend parallel to each other. As illustrated in FIG. 11, surgical instruments 200 can also be positioned in close parallel proximity to one another as housing 102 of instrument drive units 100 are coplanar with one another.

Figure 12:
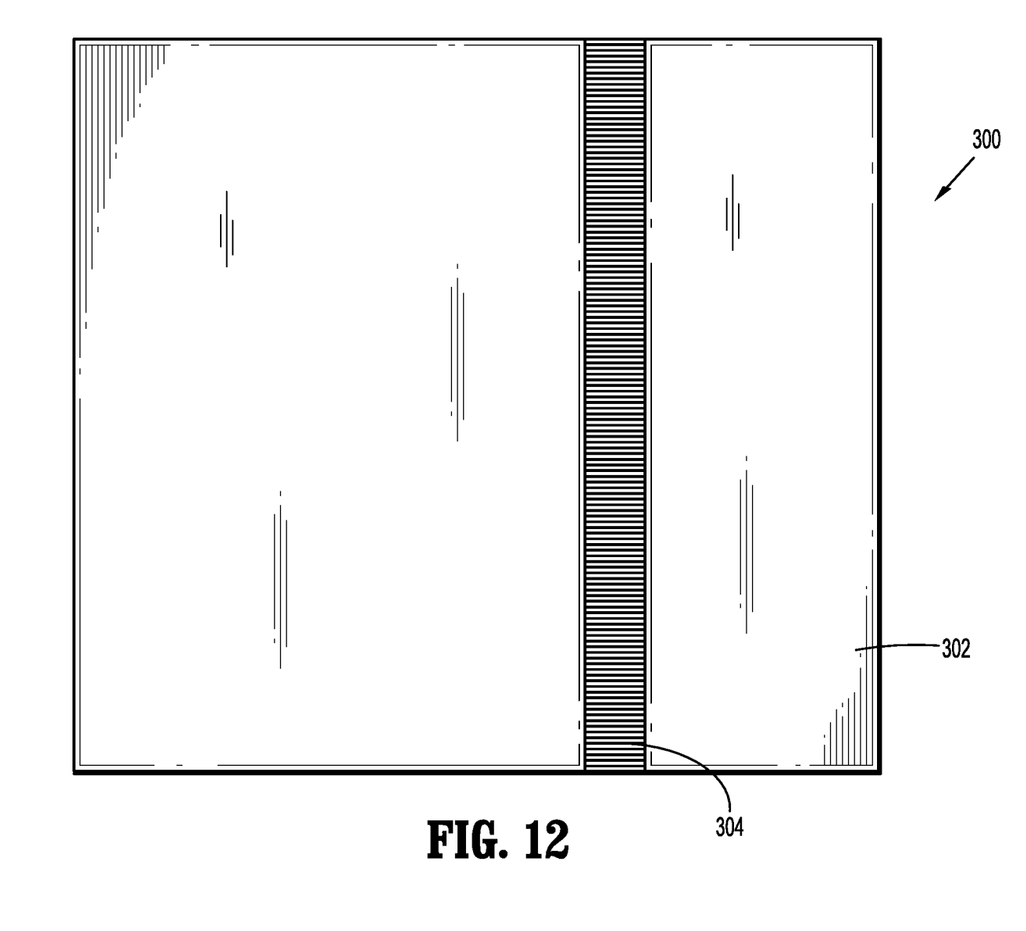
FIG. 12 is a top view of a protective barrier according to an embodiment of the present disclosure.
Figure 13:
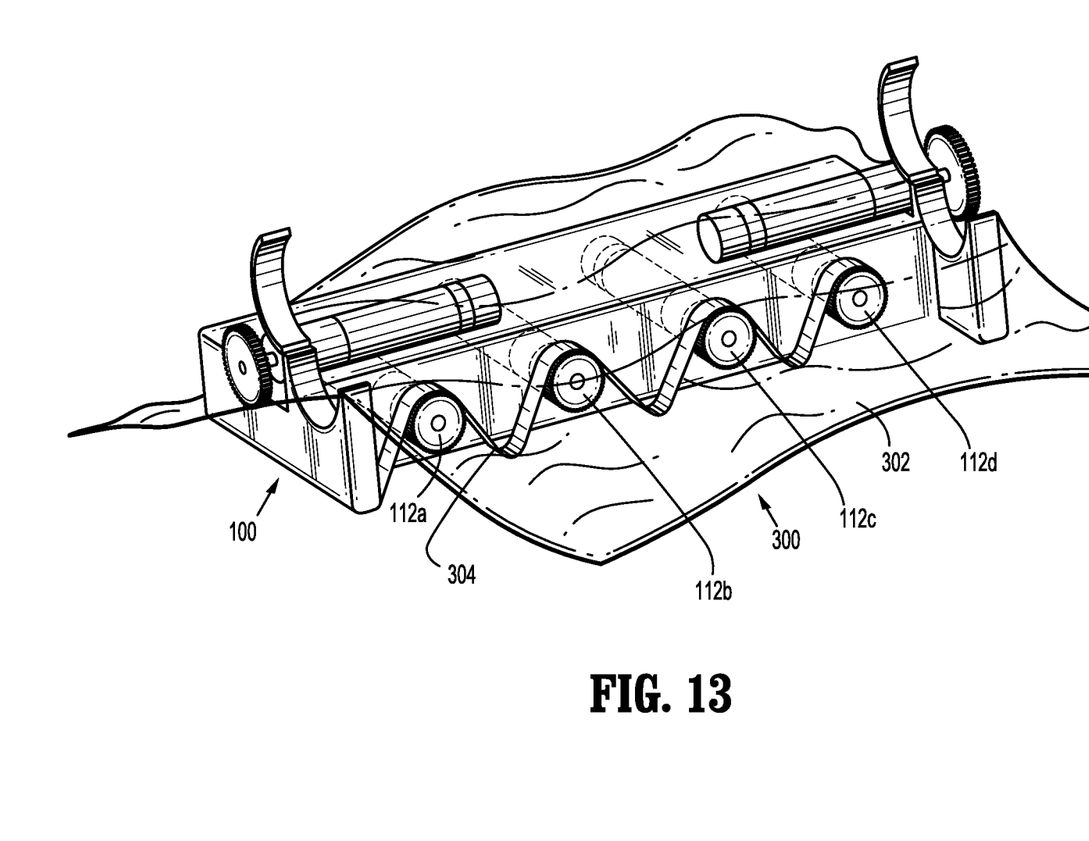
FIG. 13 is a side perspective view of the instrument drive unit shown in FIG. 3 and the protective barrier shown in FIG. 12.
Figure 14:
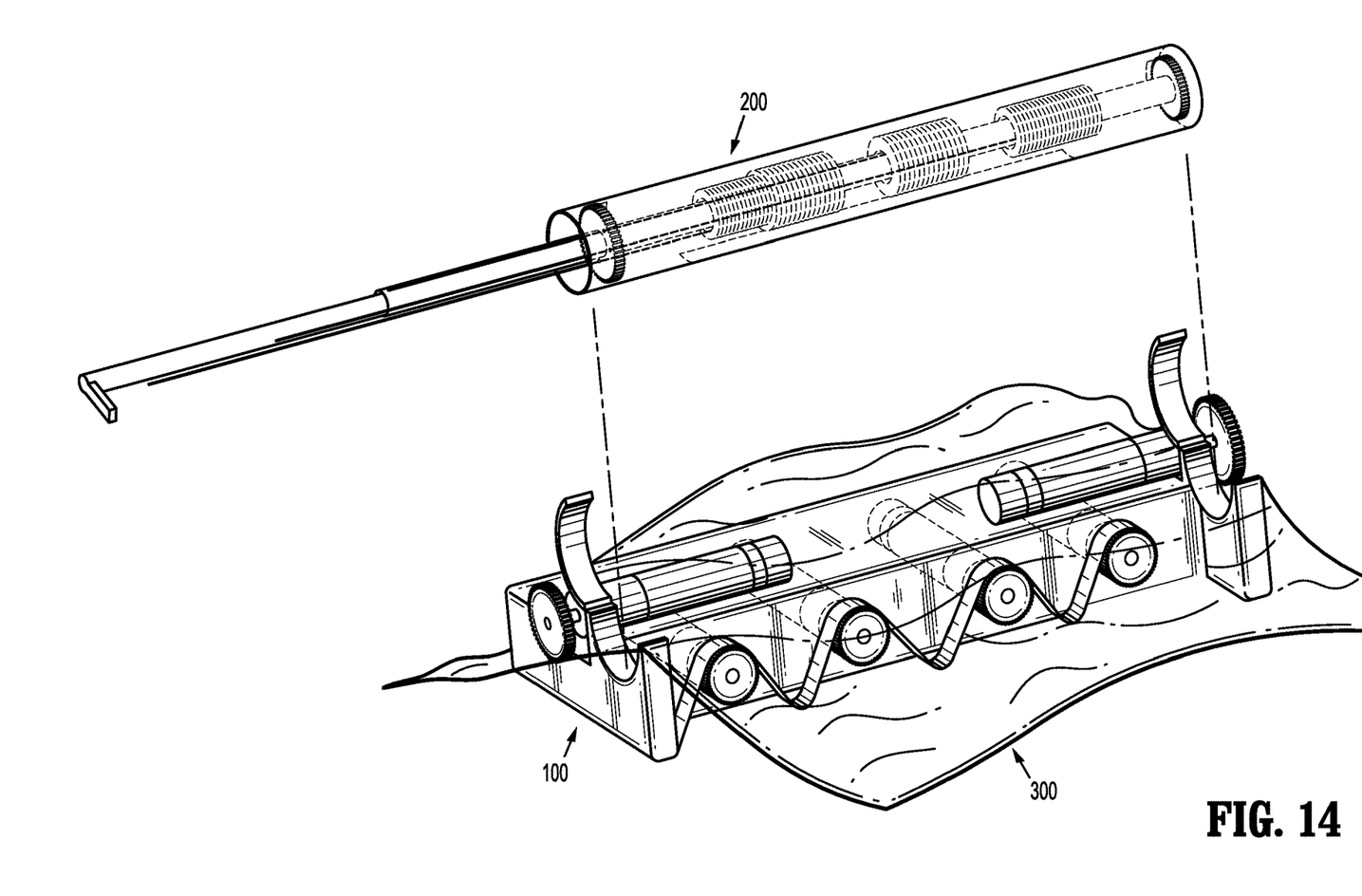
FIG. 14 is a side perspective view of the instrument drive unit and protective barrier shown in FIG. 13 and the surgical instrument shown in FIG. 4, prior to attachment of the surgical instrument to the instrument drive unit.

With reference now to FIGS. 12-14, as noted above, to maintain a sterile interface between instrument drive unit 100 and surgical instrument 200 during a surgical procedure, a protective barrier or drape 300 is received between instrument drive unit 100 and surgical instrument 200. More particularly, prior to attaching surgical instrument 200 to instrument drive unit 100, protective barrier 300 is placed over housing 102 of instrument drive unit 100.

With particular reference to FIG. 12, protective barrier 300 includes a sheet 302 and a belt 304 securely attached to or integrally formed with sheet 302. In embodiments, sheet 302 is formed of flexible polymeric material. Sheet 302 may be transparent or translucent. Belt 304 may be formed of the same or different material forming sheet 302. Belt 304 may include teeth or other texturing to facilitate engagement between drive gears 110 of instrument drive unit 100 and circular racks 210 of surgical instrument 200.

With particular reference now to FIG. 13, prior to attaching surgical instrument 200 to instrument drive unit 100, protective barrier 300 is draped over housing 102 of instrument drive unit 100 such that belt 304 of protective barrier 300 aligns with drive gears 112a, 112b, 112c, 112d of instrument drive unit 100. Sufficient slack is provided in protective sheet 300 between drive gears 112a, 112b, 112c, 112d of instrument drive unit 100 to permit the circular racks 210a, 210b, 210c, 210d of surgical instrument 200 to move through an operable range of movement. In embodiments, the range of movement is plus or minus one inch (+/−1"). As shown, protective barrier 300 is dimensioned to cover housing 102 and extend over and between flanges 106a, 106b of instrument drive unit 100. Alternatively, protective barrier 300 extends beyond housing 102 and flanges 106a, 106b of instrument drive unit 100 and may cover, in part or in whole, robotic arm 2 (FIG. 2).

Turning to FIG. 14, once protective barrier 300 is positioned over housing 102 and between flanges 106a, 106b of instrument drive unit 100 and belt 304 is aligned with drive gears 112 of instrument drive unit 100, surgical instrument 200 is attached to instrument drive unit 100 in the manner described above. The slack in protective barrier 300 provided between drive gears 112a, 112b, 112c, 112d permits operation of instrument drive unit 100 and surgical instrument 200 in the manner described above. After detaching surgical instrument 200 from instrument drive unit 100, protective barrier 300 is removed from instrument drive unit 100 and disposed of in a traditional manner.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical assembly, comprising:
   a surgical instrument including:
     an elongate body;
     an end effector extending distally from the elongate body; and
     first and second racks rotatably fixed and longitudinally movable relative to the elongate body, the first rack being slidably receivable within the second rack;
     a first cable extending distally from the first rack; and
     a second cable extending distally from the second rack, wherein each of the first cable and the second cable operably extends to the end effector of the surgical instrument.

2. The surgical assembly according to claim 1, further comprising
   an instrument drive unit configured to operatively and releasably support the surgical instrument, the instrument drive unit including:
     a first drive motor operably connected to the first rack for longitudinally moving the first rack relative to the elongate body; and
     a second drive motor operably connected to the second rack for longitudinally moving the second rack relative to the elongate body.

3. The surgical assembly according to claim 2, wherein the first drive motor includes a first drive gear for engaging the first rack and the second drive motor includes a second drive gear for engaging the second rack.

4. The surgical assembly according to claim 3, wherein the surgical assembly includes third and fourth racks, the fourth rack is slidably receivable within the third rack.

5. The surgical assembly according to claim 4, wherein the instrument drive unit includes a third motor for operable connection to the third rack and a fourth motor for operable connection to the fourth rack.

6. The surgical assembly according to claim 5, wherein the surgical assembly includes a third cable extending distally from the third rack and a fourth cable extending distally from the fourth rack.

7. The surgical assembly according to claim 2, wherein the surgical instrument further includes a first rotation gear fixedly supported on the elongate body for facilitating rotation of the elongate body about a longitudinal axis of the elongate body.

8. The surgical assembly according to claim 7, wherein the instrument drive unit includes a first rotation motor for operable connection to the first rotation gear for effecting rotation of the elongate body about the longitudinal axis of the elongate body.

9. The surgical assembly according to claim 8, wherein the instrument drive unit includes a first rotation gear connected to the first rotation motor and operably connected to the first rotation gear of the surgical instrument for effecting rotation of the elongate body about the longitudinal axis of the elongate body.

10. The surgical assembly according to claim 9, wherein the first rotation gear includes a plurality of openings for slidably receiving cables therethrough.

11. The surgical assembly according to claim 2, wherein the instrument drive unit includes a housing and a pair of flanges extending outwardly from the housing of the instrument drive unit, each flange defining a recess for selectively receiving the surgical instrument such that the surgical instrument is offset from the housing of the instrument drive unit.

12. The surgical assembly according to claim 11, wherein the instrument drive unit includes a pair of latches for selectively securing the surgical instrument within the recesses formed in the flanges of the instrument drive unit.

13. The surgical assembly according to claim 2, further including a protective barrier operably received between the instrument drive unit and the surgical instrument.

14. The surgical assembly according to claim 13, wherein the protective barrier includes a belt configured for alignment with the first and second racks of the surgical instrument when the surgical instrument is engaged with the instrument drive unit.

15. The surgical assembly according to claim 13, wherein the protective barrier is dimensioned to cover at least the instrument drive unit.

16. A surgical assembly, comprising:
a surgical instrument including:
an elongate body; and
first and second racks rotatably fixed and longitudinally movable relative to the elongate body, wherein the first rack is slidably receivable within the second rack;
an instrument drive unit configured to operatively and releasably support the surgical instrument, the instrument drive unit including:
a first drive motor operably connected to the first rack for longitudinally moving the first rack relative to the elongate body; and
a second drive motor operably connected to the second rack for longitudinally moving the second rack relative to the elongate body; and
a protective barrier received between the surgical instrument and the instrument drive unit.

17. The surgical assembly according to claim 16, wherein the protective barrier includes a belt configured for alignment with the first and second racks of the surgical instrument when the surgical instrument is engaged with the instrument drive unit.

18. The surgical assembly according to claim 17, wherein the belt of the protective barrier includes a textured surface to facilitate engagement with the first and second racks of the surgical instrument.

19. The surgical assembly according to claim 16, wherein the protective barrier is dimensioned to cover at least the instrument drive unit.

* * * * *